United States Patent [19]

Scherer

[11] 4,173,654
[45] Nov. 6, 1979

[54] NOVEL FLUOROHYDROCARBONS

[75] Inventor: Kirby V. Scherer, Santa Monica, Calif.

[73] Assignee: California Institute of Technology, Pasadena, Calif.

[21] Appl. No.: 756,011

[22] Filed: Jan. 3, 1977

[51] Int. Cl.² .................. A61K 31/02; A61K 31/035; C07C 19/08

[52] U.S. Cl. .................................. 424/350; 260/653; 260/653.3; 424/351; 252/62.2

[58] Field of Search ............................. 260/653, 653.3; 424/350, 351

[56] References Cited

U.S. PATENT DOCUMENTS

| | | | |
|---|---|---|---|
| 3,167,592 | 1/1965 | Hauptschein et al. | 260/653 |
| 3,317,618 | 5/1967 | Haszeldine | 260/653 |
| 3,962,358 | 6/1976 | Halasz | 260/653 |

FOREIGN PATENT DOCUMENTS 1130063  10/1968  United Kingdom ..................... 260/653

Primary Examiner—Sam Rosen
Attorney, Agent, or Firm—Marvin E. Jacobs

[57] ABSTRACT

Novel fluorohydrocarbons include a fluoroalkyl unit terminating in a tertiary carbon atom which is directly linked to an aliphatic moiety of the compound. The compounds contain at least 9 carbon atoms and usually no more than 13 carbon atoms. The compounds are synthesized by addition of a fluoride atom to the tertiary carbon atom of a fluorocarbon material to form a carbanion followed by alkylation of the carbanion. The fluorohydrocarbons will find use as blood substitutes or as electronic fluids.

11 Claims, No Drawings

NOVEL FLUOROHYDROCARBONS

ORIGIN OF THE INVENTION

The invention described herein was made in the performance of work under a NASA contract and is subject to the provisions of Section 305 of the National Aeronautics and Space Act of 1968, Public Law 83-568 (72 Stat. 435; 42 USC 2457).

BACKGROUND OF THE INVENTION

1. Field of the Invention

The present invention relates to novel fluorohydrocarbons, to their synthesis and use.

2. Description of the Prior Art

Fluorocarbon compounds due to their inertness have found use as electronic coolant or leak testing fluids. Other compounds having good solubility for oxygen have been investigated as artificial blood substitutes. However, the present fluorocarbons are unduly expensive due to the high content of fluorine and the method of synthesis. Furthermore, the principal industrial processes employed in their synthesis, namely electrochemical fluorination or cobalt trifluoride fluorination do not result in pure substances but mixtures of compounds containing impurities and incompletely fluorinated compounds. Pure substances of known structure are desired for clinical applications.

Another problem with fluorocarbon materials is that the excellent inertness of these materials prevents their active excretion through metabolic processes so that there appears to be no mechanism for their elimination from the body, other than by diffusion to and evaporation through the skin or lungs. Even though these chemicals are inert there is a risk in allowing them to remain indefinitely in body tissues.

It has recently been proposed that by choosing fluorochemicals of sufficiently high vapor pressure their eventual elimination via the lungs and skin can be assured. While such an approach has merit it appears likely that in large animals such as dogs and probably man enough of these chemicals will be absorbed in depot fat or in brain or spinal cord lipids from which their subsequent clearance will be very slow indeed. Since many "inert" fluorochemicals have anesthetic properties, subtle behavioral changes in higher mammals might result from such incorporation.

SUMMARY OF THE INVENTION

Novel fluorocarbon hybrid materials with hydrocarbon fragments are provided in accordance with the invention. The hybrid compounds are made by a synthetic route assuring production of pure substances in high yield and at low cost from readily available materials. The hybrid compounds have good oxygen and carbon dioxide solubility, exhibit high vapor pressure and will cost less than available electronic fluids or proposed blood substitute compounds.

The problem of accumulating fluorocarbon compounds within body tissue is obviated by attachment of a metabolically reactive hydrocarbon handle to the larger fluorocarbon unit so that the physical properties responsible for good oxygen solubility are retained, yet a reactive site is available in the molecule on which the body's general-purpose detoxifying enzymes can operate and attach solubilizing conjugating groups such as taurine, glycine, glutamate, sulfate or glucuronate, permitting gradual renal or hepatic excretion via known pathways. It is not required that all or even most of the hybrid compounds be excreted by this active mode since the vapor pressure of the hybrids is controlled so that a large fraction of the elimination takes place via the passive evaporative route. The hybrid compounds of the invention are unique in providing the additional metabolic mechanism of excretion to permit more rapid or more complete final clearance of the foreign compound from the body.

The metabolism of the foreign chemical can be adjusted to a half-life of days or weeks so that the blood substitute will not be eliminated before it has served its purpose and so that the detoxifying enzymes will not be overloaded. A further advantage of the hybrid compounds is that the hydrocarbon portion could also serve as the location of a $^{13}C$, $^{14}C$, $^{2}H$ or $^{3}H$ label, simplifying synthesis of labelled blood substitutes for research or as the site for attachment of a hydrophilic unit to create a highly fluorochemical-compatible surfactant for forming very stable emulsions.

The hydrocarbon moiety can be selected based on metabolic considerations. Alkanes provide a reactive site for slow enzymatic attack via $\alpha$, $\beta$, or $\omega$-hydroxylation in the liver microsomes. Thus, the alkyl side chains of barbituates and BHT, the antioxidant, are extensively hydroxylated and the compounds subsequently excreted as the more water soluble oxidized compounds or as the sulfate or glucuronide conjugates even though the R—$CH_3$ groups attacked are unactivated in any chemical sense. Saturated n-alkanes are known to be oxidized readily to fatty acids in the rat. Both primary and secondary C-H bonds can be attacked. Oxidized higher hydrocarbons at a higher oxidation state, e.g., ethers such as —$CH_2OCH_3$, alcohols such as —$CH_2OH$, or esters such as —$CH_2CO_2R$ and the like, might speed up the conjugation and excretion of the fluorochemical in case the alkane group is oxidized too slowly; on the other hand, an iso- or neo-alkyl side chain would probably be attacked more slowly.

In order to minimize toxicity or possible toxicity it is necessary that the connection between the fluoroalkyl moiety and the hydrocarbon portion of the molecule be designed to minimize the possibility of enzymatic or non-enzymatic degradation reactions proceeding past the linkage and breaking down the fluoroalkyl unit, liberating fluoride ion or toxic fluoroolefins. Such degradation is prevented in the hybrid compounds of the invention by terminating the fluoroalkyl unit in a tertiary carbon connected to a methylene atom which links the unit to the hydrocarbon portion of the hybrid molecule. Thus, as long as the connecting bond remains intact, there will be no labile fluorine atoms situated $\alpha$ to a hydrogen atom. The chemical lability of such C—F bonds is well known and probably accounts for the toxicity of partly fluorinated straight-chained compounds. Elimination of HF from such compounds would yield fluoroolefins, members of a class of compounds which is generally quite toxic and which includes the most toxic fluorochemicals outside of the nerve gases.

The novel hybrid compounds of the invention will find use as electronic test fluids, electronic cooling fluids and other fields where oxygen absorption is required such as enriched air for coal gasification. The hybrid compounds will find biologic use as a liquid/liquid extracorporeal oxygenator that carries oxygen from a gas source of bubbles to blood in a liquid/liquid interface oxygenator designed to minimize blood damage. The hybrids will also find use in liquid breathing. Fluorochemical blood substitutes have been utilized in organ perfusions to maintain the viability and function of organs or brain tissue in a fluorocarbon oxygen-carrying perfusate. Artifical blood preparations could have many applications including use as an emergency oxygen-carrying plasma expander in cases of bleeding in shock, exchange transfusion of newborns with erythroblastosis fetalis, patients in sickle-cell crisis, patients in various toxic states and patients suffering from drug overdoses and carbon monoxide poisoning; transfusion of patients whose religious convictions preclude the use of blood; major surgery requiring large amounts of blood; and priming of heart-lung and dialysis machines as well as such extracirculatory uses as lung lavage in cases of smoke inhalation and other pulmonary diseases, and topical application in skin ulcers, burns and the like.

These and many other features and attendant advantages of the invention will become apparent as the invention becomes better understood by reference to the following detailed description.

DESCRIPTION OF THE PREFERRED EMBODIMENTS

The hybrid compounds of the invention have the following essential structure:

$$R_f^{tert}-Z$$

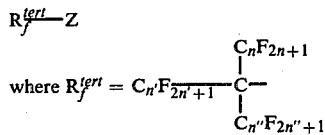

and $R_f = C_nF_{2n+1}$
$R_f' = C_{n'}F_{2n'+1}$
$R_f'' = C_{n''}F_{2n''+1}$ and $n$, $n'$, $n''$ are integers from 1 to 11 and Z is the metabolically active hydrocarbon moiety. The hybrid compound can have from 6 to 15 carbon atoms in the case of electronic fluids or other uses but for clinical blood substitutes the hybrid compound should contain from 9 to 13 carbon atoms and the vapor pressure of the compound should be <50 mm Hg at body temperature, 37° C. to 39° C., and the oxygen solubility should be at least 30 volume percent at 37.5° C.

The Z group should contain at least 2 hydrogen atoms and is preferably without unsaturation. Representative hydrocarbon groups are:

—CH$_2$—(CH$_2$)$_m$—H

—CH$_2$—(CH$_2$)$_m$—O—R

—CH$_2$—(CH$_2$)$_m$—OH

—CH$_2$—(CH$_2$)$_m$—CO$_2$R where m is an integer from 0 to 8 and R is an alkyl or substituted alkyl group containing non-interfacing, non-toxic groups such as hydrophilic groups. Straight chain alkyls are preferred from metabolic considerations.

The hybrids are synthesized by addition of a fluoride ion, F$^-$, to a perfluoroolefin to form an intermediate tertiary fluorocarbanion according to the following general reaction:

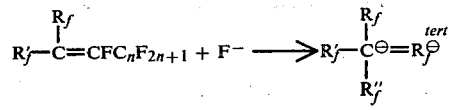

The tertiary fluorocarbon can in turn undergo alkylation or reaction with an electrophilic reagent to form a hybrid compound as follows:

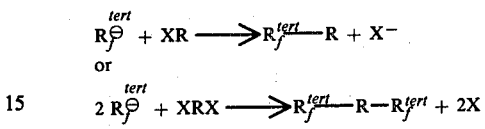

where X is an electrophilic group such as iodide or bromide.

A variety of fluoroolefins are available from anionic oliogomerization of tetrafluorethylene (TFE); hexafluoropropene (HFP), and octafluoro-2-methyl propene (perfluoroisobutene, PFIB). Representative perfluorinated compounds are shown below:

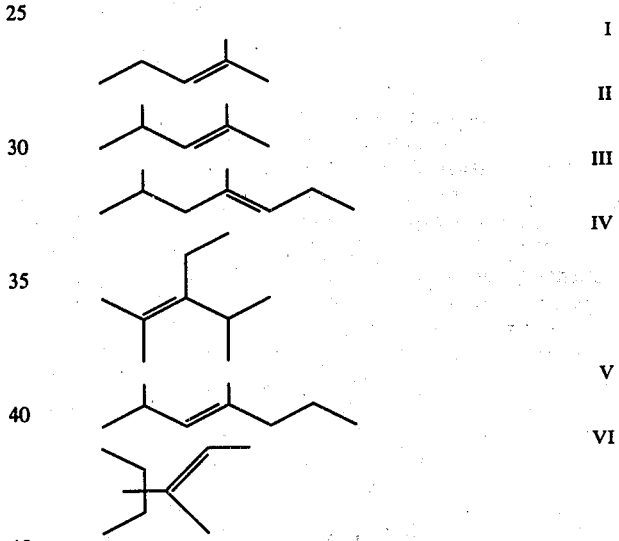

Compound I is a dimer of HFP, II is the co-dimer of HFP and PFIB, III-V are trimers of HFP and VI is a pentamer of TFE. The mechanisms of these oliogomerizations are described in R. D. Chambers, "Fluorine in Organic Chemistry," Wiley, N.Y. 1973.

The fluoride ion is present in at least a stoichiometric amount usually as a Group I metal salt such as KF, CsF, AgF or CuF. The reaction is usually conducted in a polar solvent such as dimethylformamide.

Examples of practice follow:

EXAMPLE 1

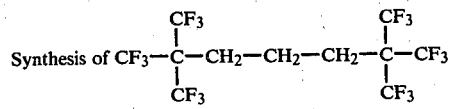

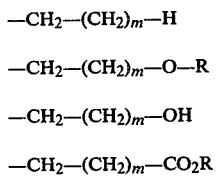

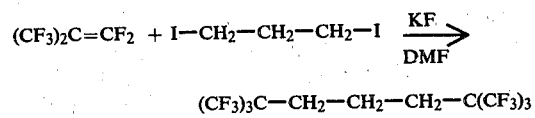

102 Grams (0.34 mol) of 1,3-diiodopropane, 41 grams (0.71 mol) of dry potassium fluoride and 200 ml. of dry dimethylformamide were placed in a 500 ml. round bottomed three necked flask equipped with a cold finger, gas inlet tube, septum and magnetic stirring. 189 Grams (0.94 mol) of perfluoroisobutene was distilled into the pot. After 6 hours of stirring with the cold finer charged, the pot contents were placed in a separatory funnel with water and the lower fluorocarbon layer removed. The crude mixture was separated on a ⅜ inch×10 foot 20% FFAP G.C. column at 150° C. with a He flow of 150 ml/min. The first of two peaks was 1,3-bis(perfluoro-tert-butyl) propane which solidified at room temperature. Sublimation of the product yielded 49 grams (0.102 mol) of material melting at 32°–33° C. This was 30% of the theoretical yield based upon starting 1,3-diiodopropane.

EXAMPLE 2

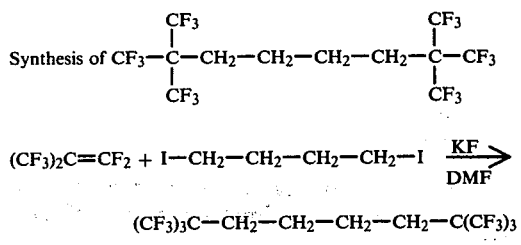

74 Grams (0.24 mol) of 1,4-diiodobutane, 40 grams (0.69 mol) of dry potassium fluoride and 200 ml. of dry dimethylformamide were placed in a 500 ml. round bottomed three necked flask equipped with a cold finger, gas inlet tube, septum and magnetic stirring. 130 grams (0.65 mol) of perfluoroisobutene was distilled into the pot. After 6 hours of stirring with the cold finger charged, the pot contents were placed into a separatory funnel with water and the lower fluorocarbon layer removed. The crude mixture was cooled to 0° C. and the solid collected by filtration. The crude 1,4-bis(perfluoro-t-butyl) butane was recrystallized twice from methanol yielding 38.4 grams (0.080 mol) of solid subliming in an open capillary at 130° C. This was a 32% yield based upon starting 1,4-diiodobutane.

EXAMPLE 3

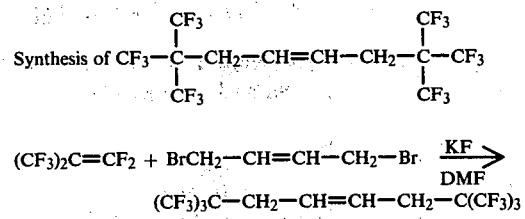

49.6 Grams (0.232 mol) of 1,4-dibromo-2-butene, 31.2 grams (0.537 mol) of dry potassium fluoride and 150 grams of dry dimethylformamide were placed in a 500 ml. round bottomed three necked flask equipped with a cold finger, gas inlet tube, septum, and magnetic stirring. 113 Grams (0.563 mol) of perfluoroisobutene was distilled into the pot. After 6 hours of stirring with the cold finger charged, the pot contents were placed in a separatory funnel with water and the lower fluorocarbon layer removed. The crude mixture was then cooled to 0° C. and the 1,4-bis(perfluoro-t-butyl)-2-butene crystallized out. The solid was separated by filtration and recrystallized from methanol. A 70% yield based upon 1,4-dibromo-2-butene was obtained, melting at β°→75° C. A second recrystallization from methanol yields pure material melting at 78.5°–79.5° C.

EXAMPLE 4

Synthesis of $CF_3-CF_2-CF_2-C(CF_3)_2-CH_2-CH=CH_2$

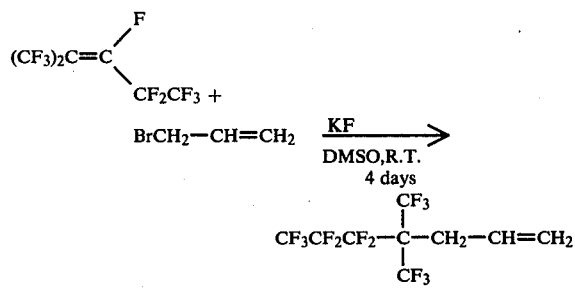

30 Grams (0.10 mol) of perfluoro-2-methyl-2-pentene, 13 grams (0.11 mol) of allyl bromide and 9 grams (0.16 mol) of dry potassium fluoride placed in a 100 ml. round bottomed single necked flask fitted with a dry tube and stirred magnetically for 4 days. The pot contents are then washed with water in a separatory funnel with water and the lower fluorocarbon layer separated. The crude product is dissolved in anhydrous ether and dried with MgSO₄. The product is filtered and fractionally distilled. 18 Grams (0.05 mol) of product was collected boiling at 119° C. This was 50% of the theoretical yield based on starting fluoroolefin.

EXAMPLE 5

Synthesis of $(CF_3)_3C-CF=CFCF_3$

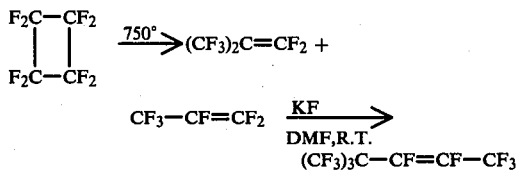

Octafluorocyclobutane is pyrolysed in a furnace with a nickel tube measuring 12 inches in length and 1 foot in diameter at 750° C. with a gas flow of 2→3 ml/min. The effluent gases, which are principally perfluoroisobutene and hexafluoropropene, are condensed with a dry ice-acetone cold finger into dry dimethylformamide containing dry potassium fluoride. A lower fluoroolefin layer forms from which the product can be distilled, bp=71°–72° C.

The above synthesis provides a novel perfluoroolefin suitable for forming hybrids. The compound is readily synthesized from available materials.

Oxygen solubilities were measured at 25° C. and 760 mm O₂ pressure for representative hybrid, fluoroolefin and prior art compounds by means of a gas chromatograph having a thermal conductivity detector and calculated from molar volume and ΔH(vap) by the method of Fedors (Polymer, Engr. Sci. 14 147 (1974). Good agreement was obtained as shown in the following table:

| Fluorochemical Material (FC) | Calculated O$_2$ Solubility cc O$_2$/100 cc FC | Measured Solubility cc O$_2$/100 cc FC | Literature Values or other data |
| --- | --- | --- | --- |
| (CF$_3$)$_3$C—(CH$_2$)$_3$CH$_3$ | 43.2 | 41.2 | D = 1.393 g/cc<br>V = 198.3 cc/mole<br>δ = 5.98 Hb<br>BP = 101.5° C./750mm |
| (CF$_3$)$_3$C—CH$_2$COC$_2$H$_5$ (C=O) | 34.6 | 34.4 | D = 1.4895<br>V = 205.5<br>δ = 7.39<br>BP = 53° C./36mm |
| (CF$_3$)$_3$C—CH$_2$CH=CH$_2$ | 44.1 | 48 | D = 1.442<br>V = 180.31<br>δ = 6.0<br>BP = 76° C./735mm |
| 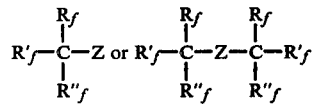 | 40.9 | 39.5 | D = 1.820<br>V = 219.8<br>δ = 6.4<br>BP = 110° C./735mm |
| (n-C$_4$F$_9$)$_3$N(FC-43) | 38.9 | 36.8 | 3M solubility data 38.9 cc O$_2$/100ccFC |

Fluorochemicals are not soluble in water and spontaneously forming emulsions are the exception. Mechanical or ultrasonic mixing in the presence of surfactants reduces the particles or droplets of fluorochemical to an extremely small size—beyond phase microscopy, probably to 0.2 μm or less in diameter and possibly to a true colloidal dispersion or microemulsion—and are dispersed sufficiently to remain stable in a "solubilized" form. In order to be useful in O$_2$ and CO$_2$ transport, the emulsions should contain stable dispersions of the fluorochemical hybrids in a concentration of at least 15-20% by volume. The pH, electrolyte concentration, osmotic and oncotic pressures are adjusted to within physiologic range.

Heat, surface coating, absorption, and the presence of air containing O$_2$ and N$_2$ all seem to alter the natural and biologic action of emulsions of fluorochemicals. It seems that carbon dioxide, itself extremely soluble in fluorochemicals, is protective to the fluorochemical, and if all steps in the preparation of the product for biologic use are carried out in a CO$_2$ atmosphere, the finished product is more acceptable biologically, is more stable, formation of fluoride ion is inhibited and the sonication into small particle sizes is facilitated. By appropriate filtration such as through a 0.2 micron membrane filter, of the emulsified product, particle sizes large enough to be biologically harmful can be removed, the solution can be sterilized (at least bacteriologically), and foreign materials removed.

The surfactant is present in the emulsion in an amount of 1 to 10% by weight usually, about 3 to 6% by weight. Suitable surfactants are egg yolk phospholipid, oxygelatin or nonionic ethylene oxide-propylene oxide polymers such as Pluronic F.68. Electrolyte can be provided by a pharmaceutically acceptable saline such as Ringer's solution.

For perfusion and blood substitute uses the emulsion preparation contains sufficient isooncotic agent, typically 3% by weight to 10% by weight to make the emulsion isooncotic and a mixture of salts and bicarbonate to give the proper ionic strength and pH.

It is to be realized that only preferred embodiments of the invention have been described and that numerous substitutions, modifications and alterations are permissible without departing from the spirit and scope of the invention as defined in the following claims.

What is claimed is:

1. A fluorochemical compound containing 9 to 15 carbon atoms selected from compounds of the formulae:

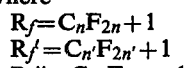

where
$R_f = C_nF_{2n}+1$
$R_f' = C_{n'}F_{2n'}+1$
$R_f'' = C_{n''}F_{2n''}+1$
and n, n' and n" are integers from 1 to 11 and Z is a hydrocarbon moiety containing at least 2 hydrogen atoms and has a methylene group connected to the tertiary carbon atom.

2. A compound according to claim 1 in which the compound contains from 9 to 13 carbon atoms and Z is a metabolically reactive hydrocarbon and the compound has a vapor pressure <50 mm Hg at 37° C. to 39° C. and an oxygen solubility of at least 30 volume percent at 37.5° C.

3. A compound according to claim 2 in which Z is selected from compounds of the formula:

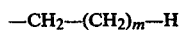

where m is an integer from 0 to 8.

4. A compound according to claim 3 in which Z contains straight chain alkyl groups.

5. A compound according to claim 1 in which at least two of n, n' and n" are 1.

6. The compound according to claim 1:

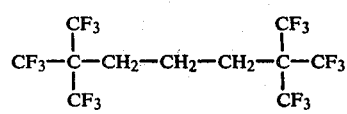

7. The compound according to claim 1:

8. The compound according to claim 1:

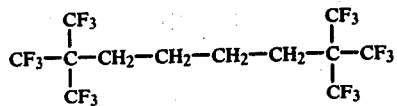

CF$_3$—CF$_2$—CF$_2$—C(CF$_3$)$_2$—CH$_2$—CH=CH$_2$

9. A method of forming compounds of claim 1 comprising the steps of reacting a fluoroolefin of the formula:

where n is an integer from 0 to 10 with a fluoride ion to form a tertiary fluorocarbanion; and
alkylating the carbanion with an electrophilic reagent.

10. An artificial blood substitute comprising a fluorohydrocarbon aqueous emulsion containing:
an effective amount of at least 15% by volume of a fluorochemical compound as defined in claim 2;
1 to 10% by weight of surfactant; and
remainder physiologically acceptable aqueous carrier.

11. An emulsion according to claim 10 further including effective amounts of osmotic, pH and oncotic agents.

* * * * *